United States Patent
Oguchi et al.

(10) Patent No.: US 11,890,592 B2
(45) Date of Patent: *Feb. 6, 2024

(54) METHOD FOR PRODUCING SILICA CARRIER, AND SILICA CARRIER

(71) Applicant: SHOWA DENKO K. K., Tokyo (JP)

(72) Inventors: Wataru Oguchi, Oita (JP); Katsuhiko Yamashita, Oita (JP); Toshihiro Kimura, Oita (JP); Daiki Shimono, Takeo (JP)

(73) Assignee: Resonac Corporation, Tokyo (JP)

( * ) Notice: Subject to any disclaimer, the term of this patent is extended or adjusted under 35 U.S.C. 154(b) by 1025 days.

This patent is subject to a terminal disclaimer.

(21) Appl. No.: 16/639,922

(22) PCT Filed: Sep. 3, 2018

(86) PCT No.: PCT/JP2018/032664
§ 371 (c)(1),
(2) Date: Feb. 18, 2020

(87) PCT Pub. No.: WO2019/049839
PCT Pub. Date: Mar. 14, 2019

(65) Prior Publication Data
US 2020/0238255 A1    Jul. 30, 2020

(30) Foreign Application Priority Data
Sep. 5, 2017  (JP) ................. 2017-170238

(51) Int. Cl.
*C01B 33/14* (2006.01)
*B01J 21/08* (2006.01)
(Continued)

(52) U.S. Cl.
CPC ............... *B01J 21/08* (2013.01); *B01J 6/001* (2013.01); *B01J 35/0026* (2013.01);
(Continued)

(58) Field of Classification Search
CPC ......... C01B 33/14; C01B 33/00; C01B 33/12; B01J 37/04; B01J 6/001; B01J 35/0026;
(Continued)

(56) References Cited

U.S. PATENT DOCUMENTS 6,187,949 B1  2/2001 Froom et al.
6,624,325 B1  9/2003 Higashi et al.
(Continued)

FOREIGN PATENT DOCUMENTS

CA   1087595 A    10/1980
EP   0 757 027 A1  2/1997
(Continued)

OTHER PUBLICATIONS

Sabde et al (NPL: Industrial Catalytic Processes for Fine and Specialty Chemicals, 2016, Chapter 4—catalyst synthesis and characterization, pp. 113-186) (Year: 2016).*

(Continued)

*Primary Examiner* — Smita S Patel
(74) *Attorney, Agent, or Firm* — Sughrue Mion, PLLC (57) ABSTRACT

A method for producing the silica carrier which includes kneading fumed silica obtained by a combustion method, silica gel obtained by a gel method, and colloidal silica obtained by a sol-gel method or a water glass method, molding the resulting kneaded product, and calcining the resulting molded body. The silica carrier has, in the measurement of pore size distribution, mesopores with a pore size of 2 to 50 nm and macropores with a pore size of more than 50 nm and 1,000 nm or less.

2 Claims, 2 Drawing Sheets

(51) Int. Cl.
*B01J 6/00* (2006.01)
*B01J 35/00* (2006.01)
*B01J 35/02* (2006.01)
*B01J 35/10* (2006.01)
*B01J 37/04* (2006.01)

(52) U.S. Cl.
CPC ......... *B01J 35/023* (2013.01); *B01J 35/1019* (2013.01); *B01J 35/1038* (2013.01); *B01J 35/1042* (2013.01); *B01J 35/1066* (2013.01); *B01J 35/1071* (2013.01); *B01J 37/04* (2013.01); *C01B 33/14* (2013.01)

(58) Field of Classification Search
CPC .. B01J 35/023; B01J 35/1019; B01J 35/1038; B01J 35/1042; B01J 35/1066; B01J 35/1071; B01J 21/08
See application file for complete search history.

(56) References Cited

U.S. PATENT DOCUMENTS

| | | | |
|---|---|---|---|
| 10,919,836 B2 * | 2/2021 | Itagaki | ............... B01J 35/1071 |
| 2005/0063890 A1 | 3/2005 | Nakanishi | |
| 2008/0255390 A1 | 10/2008 | Bosch et al. | |
| 2010/0331571 A1 | 12/2010 | Saito et al. | |
| 2013/0165608 A1 | 6/2013 | Siegel et al. | |
| 2013/0289145 A1 | 10/2013 | Miura et al. | |

FOREIGN PATENT DOCUMENTS

| | | |
|---|---|---|
| GB | 2 385 287 A | 8/2003 |
| GB | 2 398 749 A | 9/2004 |
| JP | 54-160490 A | 12/1979 |
| JP | 62-252378 A | 11/1987 |
| JP | 09-118647 A | 5/1997 |
| JP | 2000-342980 A | 12/2000 |
| JP | 2004-148177 A | 5/2004 |
| JP | 2008-513534 A | 5/2008 |
| JP | 2010-179268 A | 8/2010 |
| JP | 2015-221746 A | 12/2015 |
| JP | 2016-199444 A | 12/2016 |
| WO | 00/03967 A1 | 1/2000 |
| WO | 00/45952 A1 | 8/2000 |
| WO | 2006/032843 A1 | 3/2006 |

OTHER PUBLICATIONS

Asaki et al—JP 2010179268, see machine translation (Year: 2010).*
Jonathon Brame et al., "Surface Area Analysis Using the Brunauer-Emmett-Teller (BET) Method", U.S. Army Corps of Engineers, Engineer Research and Development Center, Environmental Quality and Technology Research Program, Sep. 2016, pp. 1-4 (4 pages total).
"Glossary: Barrett-Joyner-Halenda (BJH) Analysis", Hiden Isochema, Dec. 14, 2013, pp. 1-2 (2 pages total).
Communication dated Aug. 18, 2020, from the United States Patent and Trademark Office in U.S. Appl. No. 16/639,932.
International Search Report for PCT/JP2018/032664 dated Nov. 27, 2018 (PCT/ISA/210).
Written Opinion for PCT/JP2018/032664 dated Nov. 27, 2018 (PCT/ISA/237).
International Search Report for related PCT/JP2018/032659 dated Jan. 21, 2019 (PCT/ISA/210).
Written Opinion for related PCT/JP2018/032659 dated Jan. 21, 2019 (PCT/ISA/237).

* cited by examiner

METHOD FOR PRODUCING SILICA CARRIER, AND SILICA CARRIER

CROSS REFERENCE TO RELATED APPLICATIONS

This application is a National Stage of International Application No. PCT/JP2018/032664 filed Sep. 3, 2018, claiming priority based on Japanese Patent Application No. 2017-170238 filed Sep. 5, 2017.

FIELD

The present invention relates to a high-performance silica carrier capable of supporting a catalytic component and a method for producing the silica carrier.

BACKGROUND

It is widely known that a silica carrier is used as the catalyst carrier in the petro-chemical and petroleum refining fields. It is also known that properties of the silica carrier used in the catalyst, such as surface area, pore volume, bulk density, hydrophilicity, hydrophobicity and strength, greatly affect the performance of the catalyst. With the purpose to enhance the catalyst performance, many improvements of silica carrier have been made thus far. For example, Patent Document 1 discloses a method where a silica carrier is treated with a hydrosilane compound at a high temperature thereby eliminating the need for an activation treatment that has been conventionally carried out.

As the method for producing a silica carrier for a high-performance catalyst, Patent Document 2 discloses a method where without applying a special treatment to the silica carrier after the production, a silicic acid solution is added at the stage of production of the silica carrier while adjusting the pH of the silica gel slurry.

Patent Document 3 discloses a method where a mixture containing a water-miscible organic solvent, water and at least one metal precursor compound is reacted with a mixture of a water-miscible organic solvent, water and an acid to obtain a silica carrier that is a spherical head containing an oxide of a metal and having an average diameter, a BET specific surface area, and a pore volume in certain ranges. Patent Document 4 discloses a silica containing magnesium and a compound having a talc structure.

CITATION LIST

Patent Literature

[PTL 1] Japanese Unexamined Patent Publication (Kokai) No. 54-160490
[PTL 2] Japanese Unexamined Patent Publication (Kokai) No. 62-252378
[PTL 3] Japanese Unexamined Patent Publication (Kokai) No. 2015-221746
[PTL 4] Japanese Unexamined Patent Publication (Kokai) No. 2016-199444

SUMMARY

Technical Problem

The method described in Patent Document 1 suffers from poor versatility, requires an industrially special apparatus, and cannot be said to be an effective method. The silica carrier produced by the method described in Patent Document 2 has a large pore volume but suffers from an insufficient BET specific surface area and cannot be said to fully satisfy the properties required in industry. The silica disclosed in each of Patent Documents 3 and 4 is characterized by having excellent heat resistance and a large specific surface area, but in the case of using it as a carrier of a supported catalyst, magnesium or a compound having a talc structure, which is contained in silica, may interact with a catalyst component supported thereon to reduce the activity of the catalyst component supported thereon. It is apparent from these prior arts that a high-performance silica carrier for easily supporting a catalytic component and a method for producing the silica carrier are demanded.

An object of the present invention is to provide a silica carrier exhibiting high activity and selectivity when a catalytic component is supported thereon, and a method for producing the silica carrier.

Solution to Problem

As a result of studies, the present inventors have found that a silica carrier obtainable by kneading fumed silica obtained by a combustion method, silica gel obtained by a gel method, and colloidal silica obtained by a sol-gel method or a water glass method (ion exchange method), molding the resulting kneaded product, and calcining the resulting molded body is excellent as a carrier because of having a large BET specific surface and when a catalytic component is supported thereon, exhibits high activity and selectivity. The present invention has been accomplished based on this finding.

That is, the present invention relates to the following [1] to [10].

[1] A method for producing a silica carrier, including kneading fumed silica obtained by a combustion method, silica gel obtained by a gel method, and colloidal silica obtained by a sol-gel method or a water glass method, molding the resulting kneaded product, and calcining the resulting molded body.

[2] The method for producing a silica carrier according to [1], wherein the blending amount of fumed silica is from 5 to 50 parts by mass, the blending amount of silica gel is from 40 to 90 parts by mass, and the blending amount of the solid content of colloidal silica is from 5 to 30 parts by mass.

[3] The method for producing a silica carrier according to [1] or [2], wherein the calcining temperature is from 300 to 1,000° C.

[4] A silica carrier having, in the measurement of pore size distribution, mesopores with a pore size of 2 to 50 nm and macropores with a pore size of more than 50 nm and 1,000 nm or less.

[5] The silica carrier according to [4], wherein in the pore size distribution by mercury intrusion porosimetry, the pore volume of macropores is from 0.05 to 0.50 cc/g.

[6] The silica carrier according to [4] or [5], wherein the BET specific surface area is from 200 to 500 m$^2$/g.

[7] The silica carrier according to any one of [4] to [6], wherein the bulk density is from 300 to 700 g/L.

[8] The silica carrier according to any one of [4] to [7], wherein the average pore size of mesopores by the BJH method is from 3 to 16 nm.

[9] The silica carrier according to any one of [4] to [8], wherein the particle diameter is from 2 to 8 mm.

[10] The silica carrier according to any one of [4] to [9], which is obtained by the method according to any one of [1] to [3].

Advantageous Effects of Invention

When a catalytic component, such as transition metal, heteropolyacid and noble metal, is supported on the silica carrier of the present invention, a high-performance catalyst for use in the production of ethyl acetate by the reaction of ethylene and acetic acid, etc., can be obtained.

BRIEF DESCRIPTION OF DRAWINGS

FIG. 1A graph illustrating the pore size distribution by the BJH method of the silica carriers of Example 1 and Comparative Examples 4 to 6.

FIG. 2A graph illustrating the pore size distribution by mercury intrusion porosimetry of the silica carriers of Examples 1 to 3 and Comparative Examples 4 and 5.

FIG. 3A graph illustrating the relationship between the specific surface area and the reaction activity (STY) of Catalysts B. C and E to H and Comparative Catalysts P, Q, S and T.

DESCRIPTION OF EMBODIMENTS

Preferred embodiments of the present invention are described below, however, the present invention is not limited only to these embodiments, and it should be understood that various applications are possible within the spirit and scope of implementation of the present invention.

(Silica Carrier)

In general, synthetic amorphous silica is produced by either a dry process or a wet process. The combustion method of burning silicon tetrachloride in a hydrogen flame in the presence of oxygen is classified into the dry process, and a gel method of allowing the neutralization reaction of sodium silicate and a mineral acid to proceed in an acidic pH region and thereby causing aggregation in the state of growth of primary particles being suppressed, a sol-gel method of carrying out hydrolysis of alkoxysilane, and a water glass method of preparing active silicic acid by ion-exchanging of sodium silicate and growing particles in a seed particle-containing aqueous solution at an adjusted pH under heating, are classified into the wet process. In general, silica obtained by a combustion method is referred to as fumed silica, silica obtained by a gel method is referred to as silica gel, and silica after dispersing silica particles obtained by a sol-gel method or a water glass method in a medium, such as water, is referred to as colloidal silica.

A silica carrier of one embodiment is obtainable by kneading fumed silica obtained by a combustion method, silica gel obtained by a gel method, and colloidal silica obtained by a sol-gel method or a water glass method, molding the resulting kneaded product, and calcining the resulting molded body.

In the case of kneading fumed silica, silica gel and colloidal silica and subjecting the kneaded product to molding process and calcining, for example, the sizes of primary particle and secondary particle of the silica carrier after calcining and the internal state of a porous body are changed by the blending ratio of respective components, the kneading method, the calcining conditions, etc., and therefore, the high-order structure of the silica carrier of the present invention cannot be specified. The composition formula of the silica carrier is $SiO_2$.

There is no limit on the fumed silica, and a general fumed silica can be used. Examples of the commercially available fumed silica may include AEROSIL (trademark) produced by Nippon Aerosil Co., Ltd., REOLOSIL (trademark) produced by Tokuyama Corporation. and CAB-O-SIL (trademark) produced by Cabot Corporation. The commercially available fumed silica includes hydrophilic and hydrophobic grades, and both can be used. A typical fumed silica is characterized by having, as physical property values, for example, a primary particle diameter of 7 to 40 nm and a specific surface area of 50 to 500 $m^2/g$, being not porous but being amorphous with no internal surface area having a high purity of 99% or greater in terms of silicon oxide, and containing substantially no metal and no heavy metal.

There is no limit also on the silica gel, and a general silica gel can be used. Examples of the commercially available silica gel may include NIPGEL produced by Tosoh Silica Corporation. MIZUKASIL produced by Mizusawa Industrial Chemicals, Ltd., CARiACT produced by Fuji Silysia Chemical Ltd., and SUNSPHERE produced by AGC Si-Tech Co., Ltd. In general, silica gel is produced using, as a raw material, sodium silicate that is obtainable by mixing and melting silica sand ($SiO_2$) and soda ash ($Na_2CO_1$) and dissolving the obtained sodium silicate glass (cullet) in water, by carrying out a reaction of sodium silicate with a mineral acid, such as sulfuric acid, under acidic conditions, and causing aggregation in the state of growth of primary particles being suppressed, thereby gelling the entire reaction solution. The physical properties of the silica gel are not particularly limited, but the silica gel is characterized in that the primary particle is small, the specific surface area is high, and the secondary particle is hard. Examples of specific physical properties of the silica gel include a BET specific surface area of 200 to 1,000 $m^2/g$, a secondary particle diameter of 1 to 30 μm, and a pore volume of 0.3 to 2.5 mL/g as measured by a nitrogen gas adsorption method (BJH method). The higher the purity of silica gel, the better, and the purity is preferably 95 mass % or greater, more preferably 98 mass % or greater.

The colloidal silica is also not particularly limited, and a general colloidal silica can be used. Examples of the commercially available colloidal silica may include SNOWTEX (trademark) produced by Nissan Chemical Corporation, SILICADOL produced by Nippon Chemical Industrial Co., Ltd., ADELITE produced by ADEKA Corporation. CAB-O-SIL (trademark) TG-C Colloidal Silica produced by Cabot Corporation, and QUARTRON produced by Fuso Chemical Co., Ltd. The colloidal silica is obtained by dispersing silica line particles in a medium, such as water. The production method for colloidal silica includes a water glass method and a sol-gel method by the hydrolysis of alkoxysilane, and a colloidal silica produced by either production method can be used. A colloidal silica produced by a water glass method and a colloidal silica produced by a sol-gel method may be used in combination. Typical physical properties of the colloidal silica include a particle diameter of 4 to 80 nm and a solid content concentration of silica dispersed in water or an organic solvent of 5 to 40 mass %. The impurity concentration in the colloidal silica may affect the catalytic active component supported thereon and is therefore preferably lower. The silica purity in the solid content is preferably 99 mass % or greater, more preferably 99.5 mass % or greater.

The silica carrier can be obtained by kneading fumed silica, silica gel, and colloidal silica, molding the resulting kneaded product, and calcining the molded body. At the time of kneading, an appropriate additive may be added. The blending ratio of fumed silica, silica gel and colloidal silica is preferably set to be from 5 to 50 parts by mass of fumed silica, from 40 to 90 pans by mass is silica gel, and from 5 to 30 parts by mass of the solid content of colloidal silica, more preferably from 15 to 40 parts by mass of fumed silica, from 45 to 70 parts by mass of silica gel, and from 5 to 15 parts by mass of the solid content of colloidal silica.

At the time of mixing of fumed silica, silica gel, and colloidal silica, water or an additive may be added with the purpose of, for example, improving the moldability and enhancing the strength of the final silica carrier. The additive is not particularly limited, and an additive employed when producing a general ceramic molded material may be used. A binder, a plasticizer, a dispersant, a lubricant, a wetting agent, a defoaming agent, etc., may be used depending on the purpose.

The binder may include wax emulsion, gum arabic, lignin, dextrin, polyvinyl alcohol, polyethylene oxide, starch, methyl cellulose, Na-carboxymethyl cellulose, hydroxyethyl cellulose, sodium alginate, ammonium alginate, tragacanth gum, etc. The viscosity of the kneaded product greatly varies depending on the type and concentration of the binder and therefore, the type and amount of the binder are selected to provide a suitable viscosity for the molding method used.

The plasticizer may include glycerin, polyethylene glycol, dibutyl phthalate, etc., and can increase the flexibility of the kneaded product.

The dispersant may include, as an aqueous dispersant, carboxymethyl cellulose ammonium (CMC-$NH_4$), an oligomer of acrylic acid or an ammonium salt thereof, an anionic surfactant, ammonium polycarboxylate, wax emulsion, various amines, such as monoethylamine, pyridine, piperidine, tetramethylammonium hydroxide, etc., and may include, as a nonaqueous dispersant, a fatty acid, a fatty acid ester, a phosphoric acid ester, a synthetic surfactant, benzenesulfonic acid, etc. When such a dispersant is added, a silica carrier having a uniform microstructure after calcining can be obtained by virtue of avoiding production of agglomerated particles.

The lubricant may include a hydrocarbon-based lubricant, such as liquid paraffin, paraffin wax and chlorinated hydrocarbon, a fatty acid-based lubricant, such as stearic acid, lauric acid and a metal salt thereof, a fatty acid amide-based lubricant, etc. When the lubricant is added, molding is facilitated by virtue of reducing friction between powders and improving fluidity and in addition, the molded article is easily removed from the mold.

A wetting agent can be added so as to enhance the welting property of the powder and dispersant. The wetting agent may include, as an aqueous wetting agent, a nonionic surfactant, alcohol and glycol and may include, as a nonaqueous wetting agent, polyethylene glycol ethyl ether, polyoxyethylene ester, etc. Such a substance is readily adsorbed on the solid-liquid interface and reduces the interfacial tension to thereby improve wetting of a solid.

In the case of handling a slurried kneaded product, a defoaming agent, such as a nonionic surfactant, polyalkylene glycol derivative and polyether derivative, may also be added.

One of these additives may be used alone, or a plurality thereof may be used at the same time in combination, but it is preferable to produce an effect with as a small amount as possible, be inexpensive, be incapable of reacting with the powder, dissolve in water or a solvent, be completely decomposed in an oxidizing or non-oxidizing atmosphere, for example, at a relatively low temperature of 400° C. or less, prevent ash, particularly, an alkali metal and a heavy metal, from remaining after decomposition explosion, generate a non-toxic non-corrosive decomposition gas, and allow for re-utilization of a fragment that has not become a product.

The shape of the silica carrier is not particularly limited. The shape may include, for example, a spherical shape, a columnar shape, a hollow columnar shape, a plate-like shape, an elliptical shape, a sheet shape, and a honeycomb shape. The shape is preferably a spherical, columnar, hollow columnar or elliptical shape that facilitates filling a reactor and supporting a catalytic active component, more preferably a spherical or columnar shape.

The method for molding the silica carrier is not particularly limited, and the carrier is molded from a kneaded product containing fumed silica, silica gel and colloidal silica by any convenient method, such as mold-pouring molding, extrusion molding, tumbling granulation and spray drying. A general mold-pouring molding is also referred to as stamp molding, in which the kneaded product is put in a metal-made mold, closely packed while striking by a hammer, etc., pressurized by a piston, and then taken out of from the mold. The extrusion molding generally includes charging the kneaded product in a press, extruding through a die (spinneret), cutting to an appropriated length, and molding into a desired shape. The tumbling granulation includes dropping the kneaded product on an obliquely placed rotary disc, and rolling and growing particles on the disk into a spherical shape. The spray drying includes spraying a thick slurry into hot air to obtain a porous particle, although the particle may not be increased in size.

The size of the silica carrier is not particularly limited. The size affects, for example, the handling during production of a catalyst on which a catalytic active component is supported, or during filling with the catalyst, the differential pressure after the reactor is filled, and the reaction results of catalytic reaction and therefore, is preferably selected in consideration of these. The size of the silica carrier is determined by the calcining conditions, since shrinkage of the carrier occurs during fining of the molded body. As for the size of the silica carrier (after calcining), in the case where the silica carrier is spherical, the diameter is preferably from 0.5 mm to 12 mm, more preferably from 1 mm to 10 mm, more preferably from 2 mm to 8 mm. In the case where the silica carrier has a non-spherical shape, the size of the silica carrier (after calcining) is, as the length of a maximum dimension when the size is measured, preferably from 0.5 mm to 12 mm, more preferably from 1 mm to 10 mm, still more preferably from 2 mm to 8 mm. When the particle diameter of the silica carrier is 0.5 mm or greater, a reduction in the productivity at the time of carrier production and an increase in the pressure loss when used as a catalyst can be prevented. When the particle diameter of the silica carrier is 12 mm or less, a reduction in the reaction rate due to diffusion control and an increase of byproducts can be prevented.

The shape of the silica carrier can also be adjusted by carrying out, if desired, a treatment using Marumerizer (trademark: spheronizer machine) (Fuji Paudal Co., Ltd.), etc., before or after calcining. For example, the columnar molded body before calcining can be formed to be spherical by a treatment with the Marumerizer.

The calcining method is not particularly limited, but from the viewpoint of de-composing the additive and preventing structural disorder of silica, there is an appropriate calcining temperature range. The calcining temperature is preferably from 300° C. to 1,000° C., more preferably from 500° C. to 900° C. When the calcining temperature is in this range, the additive is completely decomposed and does not adversely affect the performance of the silica carrier. In addition, the specific surface area of the silica carrier is also enhanced. The calcining treatment can be conducted under either condition of oxidizing condition and non-oxidizing condition. For example, the calcining treatment may be carried out in an air atmosphere or may be carried out in an inert gas atmosphere, such as nitrogen gas. The calcining treatment time is also not particularly limited and can be appropriately determined according to the shape and size of the molded body, the type and amount of the additive used, etc.

The silica carrier of one embodiment has, in the measurement of pore size distribution, mesopores with a pore size of 2 to 50 nm and macropores with a pore size of more than 50 nm and 1.000 nm or less. The presence of mesopores can be confirmed by a gas adsorption method (BJH method). The presence of macropores can be confirmed by mercury intrusion porosimetry. In general, the mercury intrusion porosimetry and the gas adsorption method (BJH method) are widely used for the pore size distribution measurement of a porous substance, such as silica. According to the classification of pores of IUPAC (International Union of Pure and Applied Chemistry), macropores of 50 nm or greater and part of mesopores of 2 nm to less than 50 nm can be measured by the mercury intrusion porosimetry, and mesopores and macropores of 2 nm or less can be measured by the gas adsorption method. When the silica carrier has macropores of the above-described size, the diffusion rate of a substance within a pore is more enhanced. Use of such a silica carrier in a catalyst can be expected to enhance the activity with an increase in the main reaction rate and enhance the selectivity by virtue of suppressing sequential side reactions of the target product. When the silica carrier has mesopores of the above-described size together with macropores, the supported component can be highly dispersed, and the catalytic activity can be expected to be enhanced by virtue of increasing reaction active sites.

In the silica carrier, the distribution ratio of respective pores is not particularly limited, and an appropriate pore size distribution ratio can be selected depending on the type of reaction using the silica carrier. The pore size distribution ratio can be adjusted by the mixing ratio of fumed silica, silica gel and colloidal silica at the time of production of the silica carrier, the type and amount of the additive used, the calcining temperature, the molding method, etc.

In the pore size distribution by mercury intrusion porosimetry, the pore volume of macropores (the integrated value of all macropores' volume) of the silica carrier is preferably from 0.05 to 0.50 cc/g. The pore volume of macropores of the silica carrier is more preferably from 0.07 to 0.40 cc/g, still more preferably from 0.10 to 0.30 cc/g. When the pore volume of macropores of the silica carrier is from 0.05 to 0.50 cc/g, both the diffusion rate of substance and the strength of carrier can be satisfied.

The specific surface area by the BET method (BET specific surface area) of the silica carrier is preferably from 200 to 500 m$^2$/g. The BET specific surface area of the silica carrier is more preferably from 220 to 400 m$^2$/g, still more preferably from 240 to 400 m$^2$/g. When the BET specific surface area of the silica carrier is from 200 to 500 m$^2$/g, a sufficient reaction rate can be obtained when the silica carrier is incorporated into a catalyst.

The bulk density of the silica carrier is preferably from 300 to 700 g/L. The bulk density of the silica carrier is more preferably from 400 to 650 g/L, still more preferably from 450 to 600 g/L. When the bulk density of the silica carrier is from 300 to 700 g/L, a necessary amount of active component can be supported on the silica carrier and at the same time, the strength of carrier can be maintained.

The average pore size of mesopores by the gas adsorption method (BJH method) of the silica carrier is preferably from 3 to 16 nm. The average pore size of mesopores by the gas adsorption method (BJH method) of the silica carrier is more preferably from 4 to 14 nm, still more preferably from 5 to 12 nm. When the average pore size of mesopores by the gas adsorption method (BJH method) of the silica carrier is from 3 to 16 nm, the specific surface area by the BET method is a sufficient value.

In the present description, the pore size distribution by the gas adsorption method (BJH method), the pore size distribution by mercury intrusion porosimetry, the BET specific surface area, the bulk density, and the average pore size of mesopores by the BJH method are measured by the methods described in Examples.

EXAMPLES

The present invention is further described below by referring to Examples and Comparative Examples, but the present invention is not limited to the following Examples.

1. Production of Silica Carrier

Fumed silica, silica gel, colloidal silica, and, if desired, water and/or additives were put in a kneader and kneaded to prepare a kneaded product. Subsequently, the kneaded product was charged into an extrusion molding machine attached with a die having provided at the tip thereof a circular hole with a desired size. Furthermore, an intermediate extruded from the extrusion molding machine was cut by a cutter into a desired size to obtain a columnar molded body before calcining. The molded body before calcining was treated with Marumerizer, then preliminarily dried, and furthermore subjected to a calcining treatment at a temperature of 700° C. to 900° C. in an air atmosphere to obtain a silica carrier. Detailed conditions are described in each example.

2. Measurement of Bulk Density of Silica Carrier

The silica carrier was charged in several batches into a glass-made measuring cylinder which was tared and at the same time, the measuring cylinder containing the carrier or catalyst (a catalyst metal, etc., was supported on the carrier) was tapped at every charging. The carrier was charged until reaching just the metric volume of the measuring cylinder. Subsequently, the weight of the measuring cylinder in the state of the carrier contained therein was measured, and the bulk density of the carrier was determined by the tare and volume of the measuring cylinder.

3. Measurement of BET Specific Surface Area of Silica Carrier

The BET specific surface area by nitrogen gas adsorption of the silica carrier or catalyst was measured using a gas adsorption system (ASAP 2020) manufactured by Shimadzu Corporation. In addition, the pore size distribution of the silica carrier according to the BJH method was measured, and the average pore size of mesopores was measured.

4. Measurement of Pore Size Distribution by Mercury Intrusion Porosimetry of Silica Carrier The pore size distribution of the silica carrier according to mercury intrusion porosimetry was measured using Autopore IV9500 manufactured by Shimadzu Corporation. Furthermore, in the pore size distribution, the peak pore volume (cc/g) derived from macropores of 30 to 300 nm was measured.

5. Raw Material Silicas

The raw material silicas used are shown in Table 1.

TABLE 1

| | No. | Specific Surface Area (m²/g) | Average Pore Size (nm) | Average Particle Diameter (μm) | Purity (%) |
|---|---|---|---|---|---|
| Fumed silica | F-1 | 380 | no pore | 0.007 | 99.9 |
| | F-2 | 200 | no pore | 0.012 | 99.9 |
| Silica gel | S-1 | 500 | 6 | 5 | 99.9 |
| | S-2 | 360 | 8 | 5 | 99.9 |
| | S-3 | 300 | 10 | 5 | 99.9 |
| | S-4 | 850 | 5 | 5 | 99.9 |
| Colloidal silicas*[)] | C-1 | — | — | 0.012 | — |

*[)]Solid content: 20 mass %

Example 1

Figure 1:
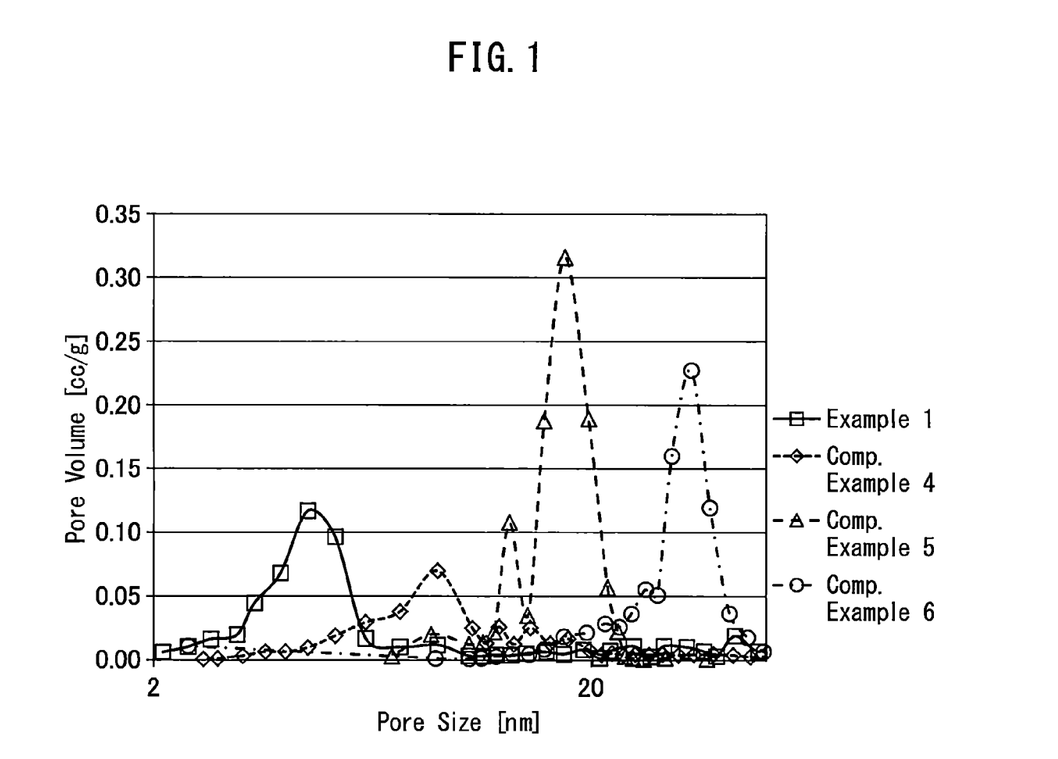
Figure 2:
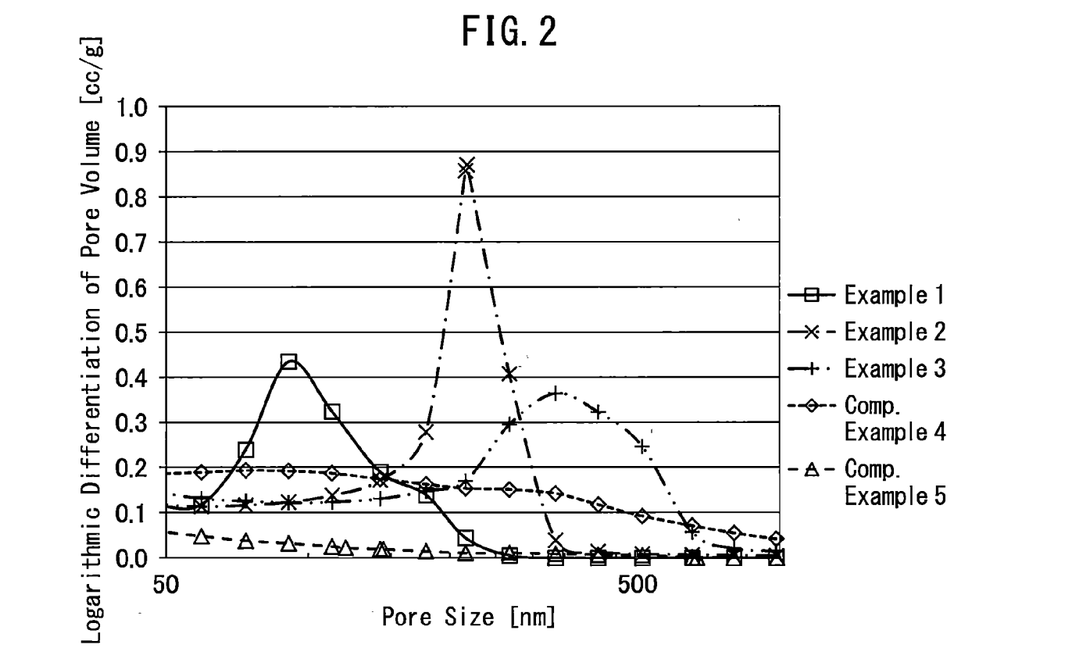

25 Parts by mass of Fumed Silica F-1, 75 parts by mass of Silica Gel S-1, and 45 parts by mass (9 parts by mass as solid content) of Colloidal Silica C-1 were kneaded in a kneader, and while observing the condition of the kneaded product, appropriate amounts of water and additives (methyl cellulose: SM-4000 produced by Shin-Etsu Chemical Co., Ltd., 10 parts by mass: resin-based binder: Serander (trademark) YB-132A produced by Yuken Industry Co., Ltd., 5 parts by mass) were added. The mixture was further kneaded to obtain a kneaded product. The kneaded product was then charged into an extrusion molding machine attached with a die having provided thereon a circular hole of 6 mmφ and by extruding the kneaded product, extrusion molding was carried out while cutting the extruded intermediate by a cutter such that the length thereof is the same length as the diameter of the circular hole. The resulting molded body before calcining was formed into a spherical shape by Marumerizer (trademark), then dried at 70° C. for 24 hours or longer, furthermore calcined at about 820° C. in an air atmosphere, and cooled to obtain Silica Carrier A. The measurement results of BET specific surface area, average pore size by the BJH method, bulk density, etc., of the obtained Silica Carrier A are shown in Table 2. In addition, FIG. 1 illustrates the pore size distribution by the BJH method of Silica Carrier A. and FIG. 2 illustrates the measurement results of the pore size distribution by mercury intrusion porosimetry.

Examples 2 to 11

Silica Carriers B to K were obtained in the same manner as in Example 1, except that the types and amounts of fumed silica, silica gel and colloidal silica and the calcining temperature were changed as shown in Table 2. However, in Examples 4 to 11, a die having provided thereon a circular hole of 3 mmφ was used. The measurement results of BET specific surface area, average pore size by the BJH method, bulk density, etc., of each of the obtained silica carriers are shown in Table 2. In addition. FIG. 2 illustrates the measurement results of the pore size distribution by mercury intrusion porosimetry of Silica Carriers B and C.

Comparative Example 1

Production of the silica carrier of Comparative Example 1 was tried in the same manner as in Example 1, except for not using colloidal silica, but a molded body usable as a carrier was not obtained.

Comparative Example 2

Production of the silica carrier of Comparative Example 2 was tried in the same manner as in Example 1, except for not using fumed silica, but a molded body usable as a carrier was not obtained.

Comparative Example 3

Production of the silica carrier of Comparative Example 3 was tried in the same manner as in Example 1, except for not using silica gel, but a molded body usable as a carrier was not obtained.

Comparative Example 4

The measurement results of BET specific surface area, average pore size by the BJH method, bulk density, etc., of commercially available silica carrier KA-160 (Silica Carrier P) produced by Clariant Catalyst Corporation, which is a natural product-derived silica gel, are shown in Table 3. In addition. FIG. 1 illustrates the pore size distribution by the BJH method of Silica Carrier P. and FIG. 2 illustrates the measurement results of the pore size distribution by mercury intrusion porosimetry.

Comparative Example 5

The measurement results of BET specific surface area, average pore size by the BJH method, bulk density, etc., of silica carrier CARiACT Q-15 (Silica Carrier Q) produced by Fuji Silysia Chemical Ltd., which is a commercially available silica gel, are shown in Table 3. In addition. FIG. 1 illustrates the pore size distribution by the BJH method of Silica Carrier Q, and FIG. 2 illustrates the measurement results of the pore size distribution by mercury intrusion porosimetry.

Comparative Example 6

The measurement results of BET specific surface area, average pore size by the BJH method, bulk density, etc., of silica carrier CARiACT Q-30 (Silica Carrier R) produced by Fuji Silysia Chemical Ltd., which is a commercially available silica gel, are shown in Table 3. In addition, FIG. 1 illustrates the measurement results of the pore size distribution by the BJH method of Silica Carrier R.

Comparative Example 7

The measurement results of BET specific surface area, average pore size by the BJH method, bulk density, etc., of silica carrier CARiACT Q-10 (Silica Carrier S) produced by Fuji Silysia Chemical Ltd., which is a commercially available silica gel, are shown in Table 3.

Comparative Example 8

The measurement results of BET specific surface area, average pore size by the BJH method, bulk density, etc., of silica carrier CARiACT Q-6 (Silica Carrier T) produced by Fuji Silysia Chemical Ltd., which is a commercially available silica gel, are shown in Table 3.

TABLE 2

| No. | Silica Carrier | Particle Diameter (mm) | Fumed Silica Type | Fumed Silica Blending Amount parts by mass | Fumed Silica Blending Amount mass % | Silica Gel Type | Silica Gel Blending Amount parts by mass | Silica Gel Blending Amount mass % | Colloidal Silica Type | Colloidal Silica Blending Amount (solid content) parts by mass | Colloidal Silica Blending Amount (solid content) mass % |
|---|---|---|---|---|---|---|---|---|---|---|---|
| Example 1 | A | 6 | F-1 | 25 | 22.9 | S-1 | 75 | 68.8 | C-1 | 9 | 8.3 |
| Example 2 | B | 6 | F-1 | 25 | 22.9 | S-2 | 75 | 68.8 | C-1 | 9 | 8.3 |
| Example 3 | C | 6 | F-1 | 25 | 22.9 | S-3 | 75 | 68.8 | C-1 | 9 | 8.3 |
| Example 4 | D | 3 | F-1 | 25 | 22.9 | S-2 | 75 | 68.8 | C-1 | 9 | 8.3 |
| Example 5 | E | 3 | F-1 | 25 | 22.9 | S-1 | 75 | 68.8 | C-1 | 9 | 8.3 |
| Example 6 | F | 3 | F-1 | 10 | 9.2 | S-1 | 90 | 82.6 | C-1 | 9 | 8.3 |
| Example 7 | G | 3 | F-1 | 40 | 36.7 | S-1 | 60 | 55.0 | C-1 | 9 | 8.3 |
| Example 8 | H | 3 | F-2 | 25 | 22.9 | S-1 | 75 | 68.8 | C-1 | 9 | 8.3 |
| Example 9 | I | 3 | F-1 | 25 | 22.9 | S-1 | 75 | 68.8 | C-1 | 9 | 8.3 |
| Example 10 | J | 3 | F-1 | 25 | 22.9 | S-1 | 75 | 68.8 | C-1 | 9 | 8.3 |
| Example 11 | K | 3 | F-1 | 25 | 22.9 | S-4 | 75 | 68.8 | C-1 | 9 | 8.3 |
| Comparative Example 1 | L | 6 | F-1 | 25 | 25.0 | S-1 | 75 | 75.0 | — | 0 | 0.0 |
| Comparative Example 2 | M | 6 | — | 0 | 0.0 | S-1 | 75 | 89.3 | C-1 | 9 | 10.7 |
| Comparative Example 3 | N | 6 | F-1 | 25 | 73.5 | — | 0 | 0.0 | C-1 | 9 | 26.5 |

| No. | Calcining Temp. (° C.) | BET Specific Surface Area (m²/g) | Average Pore Size by BJH Method (nm) | Bulk Density (g/l.) | Presence or Absence of Mesopores | Presence or Absence of Macropores | Pore Volume of Macropores (cc/g) |
|---|---|---|---|---|---|---|---|
| Example 1 | 820 | 313 | 6.6 | 548 | present | present | 0.15 |
| Example 2 | 820 | 286 | 9.4 | 438 | present | present | 0.22 |
| Example 3 | 820 | 225 | 14.5 | 386 | present | present | 0.22 |
| Example 4 | 820 | 287 | 9.4 | 439 | present | present | 0.25 |
| Example 5 | 820 | 293 | 6.6 | 567 | present | present | 0.16 |
| Example 6 | 820 | 297 | 5.5 | 619 | present | present | 0.16 |
| Example 7 | 820 | 294 | 7.4 | 551 | present | present | 0.15 |
| Example 8 | 820 | 273 | 6.4 | 593 | present | present | 0.11 |
| Example 9 | 750 | 356 | 6.5 | 507 | present | present | 0.19 |
| Example 10 | 700 | 381 | 6.5 | 481 | present | present | 0.20 |
| Example 11 | 820 | 284 | 5.4 | 686 | present | present | 0.15 |
| Comparative Example 1 | 820 | could not be molded and was unusable as a carrier | | | | | |
| Comparative Example 2 | 820 | | | | | | |
| Comparative Example 3 | 820 | | | | | | |

TABLE 3

| No. | Silica Carrier | Product name | Supplier | BET Specific Surface Area (m²/g) | Average Pore Size by BJH Method (nm) | Bulk Density (g/L) | Presence of Absence of Mesopores | Presence of Absence of Macropores | Pore Volume of Macropores (cc/g) |
|---|---|---|---|---|---|---|---|---|---|
| Comparative Example 4 | P | KA-160 | Clariant Catalyst Corporation | 151 | 10.8 | 579 | present | absent | (0.19) |
| Comparative Example 5 | Q | CARiACT Q-15 | Fuji Silysia Chemical Ltd. | 183 | 22.4 | 430 | present | absent | 0.02 |
| Comparative Example 6 | R | CARiACT Q-30 | Fuji Silysia Chemical Ltd. | 105 | 33.6 | 435 | absent | absent | 0.03 |
| Comparative Example 7 | S | CARiACT Q-10 | Fuji Silysia Chemical Ltd. | 305 | 11.5 | 423 | present | absent | 0.02 |
| Comparative Example 8 | T | CARiACT Q-6 | Fuji Silysia Chemical Ltd. | 379 | 5.2 | 623 | present | absent | 0.01 |

As apparent from FIGS. 1 and 2, in Silica Carrier A of Example 1, mesopores having a peak around 4.5 nm and macropores having a peak around 90 nm are present, and the pore volume of macropores is 0.15 cc/g. On the other hand, in Silica Carriers P and Q of Comparative Examples 4 and 5, a peak corresponding to macropores is not observed from FIG. 2.

The values calculated by integrating pore volumes of macropores in the range of more than 50 nm and 1,000 nm or less from the pore size distribution by mercury intrusion porosimetry are shown in Tables 2 and 3. In all of Silica Carriers A to K of examples, the pore volume of macropores is 0.10 cc/g or greater, but in Silica Carriers Q, S and T of Comparative Examples 5, 7 and 8, the pore volume of macropores is only less than 0.02 cc/g, and macropores are not present. Furthermore, Silica Carrier P of Comparative Example 4 is calculated to have a pore volume of macropores of 0.19 cc/g, but since a clear peak of macropores is not observed in FIG. 2, substantially no macropores are present.

<Evaluation of Catalyst Performance>

Catalysts where a heteropolyacid was supported on Silica Carriers A to C and E to H of Examples 1 to 3 and 5 to 8 and Silica Carriers P, Q, S and T of Comparative Examples 4, 5, 7 and 8 were prepared according to the following procedures and evaluated for the catalyst performance by using the catalyst in a reaction of producing ethyl acetate from ethylene and acetic acid.

(Preparation of Catalyst A)

40.7 g of commercially available Keggin-type silicotungstic acid $H_4SiW_{12}O_{40} \cdot 26H_2O$ (produced by Nippon Inorganic Colour & Chemical Co., Ltd.) was dissolved in 34.1 mL of distilled water. The obtained solution was then added to 100 mL (54.8 g) of Silica Carrier A of Example 1 and thoroughly stirred to impregnate the carrier. The carrier impregnated with the solution was transferred to a porcelain dish, air dried for 1 hours and then dried for 5 hours by a dryer adjusted to 130° C. to obtain Catalyst A.

(Preparation of Catalysts B, C and E to H and Comparative Catalysts P, Q, S and T)

Each catalyst was obtained in the same manner as in the preparation of Catalyst A, except that any of Silica Carriers B, C and E to H and Silica Carriers P. Q. S and T was used in place of Silica Carrier A.

(Catalyst Specific Surface Area)

The catalyst specific surface area of each of Catalysts A to C and E to H and Comparative Catalysts P. Q. S and T was measured as a BET specific surface area based on nitrogen gas adsorption by using a gas adsorption system (ASAP 2020) manufactured by Shimadzu Corporation.

(Production of Ethyl Acetate)

A columnar SUS316L pressure-resistant vessel having a radius of 25 mm was filled with 40 mL of each of the catalysts obtained above and after the pressure was elevated to 0.75 MPaG, the temperature was raised to 155° C. A pretreatment was carried out for 30 minutes under the conditions of nitrogen gas/acetic acid (gas)/water vapor=85.5 mol %/10.0 mol %/4.5 mol %, and SV (the volume of raw material passing through in 1 hour per L of the catalyst (L/L·h=$h^1$))=1,500 $h^1$ and thereafter, the reaction was carried out for 5 hours under the conditions of ethylene (gas)/nitrogen gas/acetic acid (gas)/water vapor=78.5 mol %/7.0 mol %/10.0 mol %/4.5 mol % and SV=1.500 $h^1$. The reaction was carried out by adjusting the reaction temperature such that out of portions formed by dividing the catalyst layer into tenths, the portion having a highest reaction temperature is at 165.0° C. The gas passed during the time period between 3 hours and 5 hours after the start of reaction was recovered in its entire amount by collecting it under ice-water cooling for a predetermined time (hereinafter, this is referred to as "condensate") and analyzed. In addition, with respect to the uncondensed gas remaining without being condensed (hereinafter, this is referred to as "uncondensed gas"), the gas flow rate was measured for the same time as that of the condensate, and a 100 mL portion thereof was taken out and analyzed. The reaction results obtained are shown in Table 4.

(Analysis Method of Condensate)

The analysis was carried out using the internal standard method under the following conditions, where the analysis solution was prepared by adding 1 mL of 1,4-dioxane as the internal standard to 10 mL of the reaction solution and a 0.2 µL portion thereof was injected.

Gas chromatography: GC-14A manufactured by Shimadzu Corporation

Column: capillary column TC-WAX (length: 30 m, inner diameter: 0.25 mm, film thickness: 0.5 µm)

Carrier gas: nitrogen (split ratio: 36, column flow rate: 1.2 ml/min)

Temperature conditions: The detector and vaporization chamber were set at a temperature of 200° C., and the column temperature was kept at 40° C. for 7 minutes from the start of analysis, then raised to 200° C. at a temperature rise rate of 10'C/min. and kept at 200° C. for 5 minutes.

Detector FID ($H_2$ pressure: 49 kPa, air pressure: 98 kPa)

(Analysis Method of Uncondensed Gas)

The analysis was carried out using the absolute calibration curve method under the following conditions, where 100 mL of the uncondensed gas was sampled and the whole amount thereof was flowed to a 1-mL gas sampler attached to the gas chromatograph.

1. Diethyl Ether. Ethyl Acetate, and Ethanol

Gas chromatograph: 7890A manufactured by Agilent Technologies

Column: Agilent J&W GC column DB-624

Carrier gas: He (flow rate: 1.7 mL/min)

Temperature conditions: The detector and vaporization chamber were set at a temperature of 230° C. and the column temperature was kept at 40° C. for 3 minutes from the start of analysis and then raised to 200° C. at a rate of 20° C./min.

Detector. FID ($H_2$: 40 mL/min, air pressure: 400 mL/min)

2. Ethylene

Gas chromatograph: 7890A manufactured by Agilent Technologies

Column: SHIMADZU GC GasPro (30 m), Agilent J&W GC column HP-1

Carrier gas: He (flow rate: 2.7 mL/min)

Temperature conditions: The detector and vaporization chamber were set at a temperature of 230° C., and the column temperature was kept at 40° C. for 3 minutes from the start of analysis and then raised to 200° C. at a rate of 20° C./min.

Detector FID ($H_2$: 40 mL/min. air pressure: 400 mL/min)

3. Nitrogen

Gas chromatograph: 7890A manufactured by Agilent Technologies

Column: HayesepQ G3591-80004

Carrier gas: He (flow rate: 60 psi)

Temperature conditions: The detector and vaporization chamber were set at a temperature of 230° C., and the column temperature was kept at 40° C. for 3 minutes from the start of analysis and then raised to 200° C. at a rate of 20° C./min.

Detector TCD (He: 45 mL/min. air pressure: 2 mL/min)

TABLE 4

| No. | Example | | | | | | | Comparative Example | | | |
| --- | --- | --- | --- | --- | --- | --- | --- | --- | --- | --- | --- |
|  | 1 | 2 | 3 | 5 | 6 | 7 | 8 | 4 | 5 | 7 | 8 |
| Catalyst | A | B | C | E | F | G | H | P | Q | S | T |
| Silica carrier | A | B | C | E | F | G | H | P | Q | S | T |
| EtOAc[2] STY[1] (g/h · L) | 347.2 | 318.2 | 260.8 | 337.7 | 340.5 | 345.1 | 347.2 | 213.8 | 237.3 | 290.7 | 316.8 |
| DEE[3] STY[1] (g/h · L) | 17.3 | 12.1 | 6.3 | 10.7 | 11.4 | 11.2 | 12.1 | 3.3 | 2.3 | 6.7 | 9.5 |
| EtOH[4] STY[1] (g/h · L) | 8.9 | 7.9 | 6.2 | 8.5 | 8.6 | 8.7 | 8.8 | 4.1 | 4.6 | 5.8 | 7.6 |
| EtOAc Selectivity (%) | 85.3 | 87.5 | 91.0 | 88.7 | 88.3 | 88.5 | 88.0 | 92.5 | 94.1 | 91.4 | 89.1 |
| DEE Selectivity (%) | 10.1 | 7.9 | 4.9 | 6.7 | 7.0 | 6.8 | 7.3 | 3.4 | 2.1 | 4.3 | 6.3 |
| EtOH Selectivity (%) | 4.2 | 4.1 | 3.8 | 4.2 | 4.2 | 4.2 | 4.2 | 3.4 | 3.5 | 4.0 | 4.1 |
| Catalyst specific surface area (m²/mL) | 148.1 | 120.9 | 98.3 | 143.3 | 159.9 | 138.7 | 147.3 | 79.4 | 92.0 | 130.4 | 213.3 |

[1] Space-time yield,
[2] ethyl acetate,
[3] diethyl ether, and
[4] ethanol.

Figure 3:
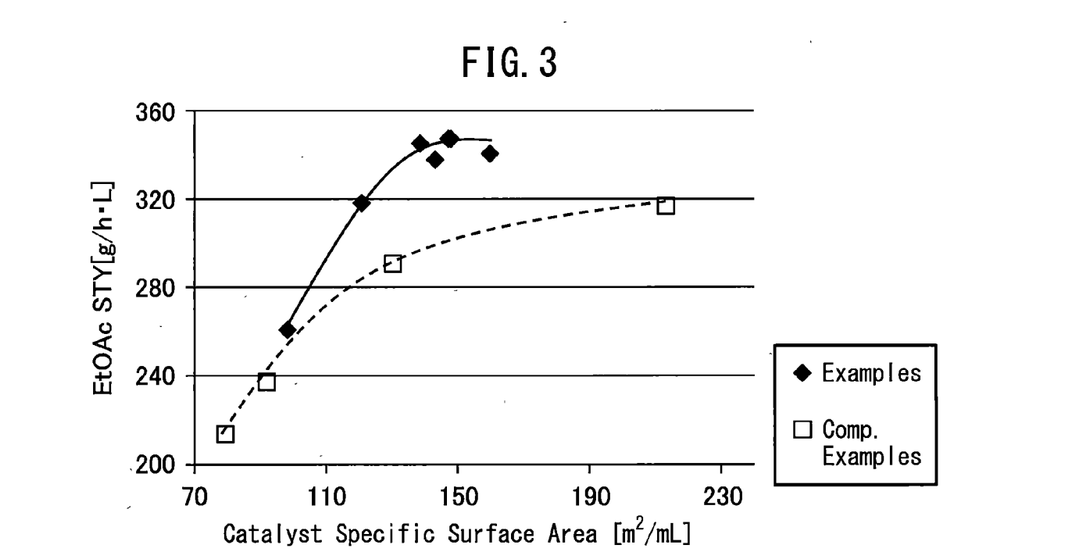

It is known that there is generally correlation between the specific surface area and the activity of the catalyst. FIG. 3 graphically illustrates the relationship between the specific surface area and the reaction activity (STY of ethyl acetate) of Catalysis B. C and E to H and Comparative Catalysts P, Q, S and T. As seen from FIG. 3, the characteristic pore size distribution of the catalyst supported on the silica carrier of the Examples reveals that the catalyst exhibits higher activity with the same specific surface area, compared with the catalyst using a commercially available silica carrier (Silica Carriers P, Q. S and T).

In addition, it is seen that in Examples 1 and 2 and Examples 4 to 7 where the silica carrier has a large pore volume of macropores and a large BET specific surface area at the same time, the catalyst exhibits higher activity, compared with the catalyst using a commercially available silica carrier (Silica Carriers P. Q. S and T).

INDUSTRIAL APPLICABILITY

The present invention provides a high-performance silica carrier usable for a supported catalyst and is useful in industry.

The invention claimed is:

1. A method for producing a silica carriers comprising kneading a fumed silica obtained by a combustion method, a silica gel obtained by a gel method, and a colloidal silica obtained by a sol-gel method or a water glass method, molding the resulting kneaded product, and calcining the resulting molded kneaded product,
wherein a blending amount of the fumed silica is from 5 to 50 parts by mass, a blending amount of the silica gel is from 40 to 90 parts by mass, and a blending amount of a solid content of the colloidal silica is from 5 to 30 parts by mass, based on total parts by mass of the silica carrier.

2. The method for producing a silica carrier according to claim 1, wherein the calcining is at a temperature from 300 to 1,000° C.

* * * * *